United States Patent [19]

Lemke

[11] Patent Number: 5,460,712
[45] Date of Patent: Oct. 24, 1995

[54] COKER/VISBREAKER AND ETHYLENE FURNACE ANTIFOULANT

[75] Inventor: Harald K. Lemke, Sugar Land, Tex.

[73] Assignee: Nalco Chemical Company, Naperville, Ill.

[21] Appl. No.: 347,762

[22] Filed: Nov. 30, 1994

[51] Int. Cl.[6] .............................. C10G 9/12; C07C 7/20
[52] U.S. Cl. .................................. 208/48 AA; 208/48 R; 585/3; 585/950
[58] Field of Search ........................... 208/48 AA, 48 R, 208/47; 585/3, 950

[56] References Cited

U.S. PATENT DOCUMENTS

| | | | |
|---|---|---|---|
| 4,024,048 | 5/1977 | Shell et al. | 208/48 AA |
| 4,024,049 | 5/1977 | Shell et al. | 208/48 AA |
| 4,024,050 | 5/1977 | Shell et al. | 208/48 AA |
| 4,024,051 | 5/1977 | Shell et al. | 208/348 |
| 4,105,540 | 8/1978 | Weinland | 208/48 AA |
| 4,226,700 | 10/1980 | Broom | 208/48 AA |
| 4,440,657 | 4/1984 | Metro et al. | 252/49.9 |

*Primary Examiner*—Asok Pal
*Assistant Examiner*—Bekir L. Yildirim
*Attorney, Agent, or Firm*—Robert A. Miller; James J. Drake

[57] ABSTRACT

A method of preventing fouling and coke formation on the high temperature sections of hydrocarbon processing equipment in contact with a hydrocarbon fluid which comprises adding to the hydrocarbon fluid prior to its contact with the high temperature sections of such hydrocarbon processing equipment an effective amount of a compound having the formula:

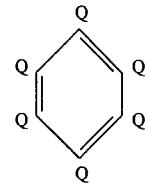

wherein Q is Z, or R with the proviso that two occurances of Q are Z, R is hydrogen, or a straight or branched alkyl group having from 1 to 7 carbon atoms, and only one or two occurances of R may be alkyl;

Z is represented by the formula:

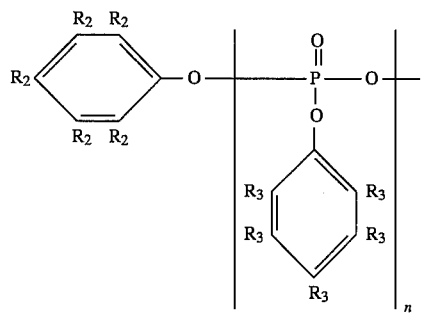

wherein $R_2$ and $R_3$ are the same as R and only one or two occurances of each of $R_2$ or $R_3$ may be alkyl, and "n" is a whole number of from 1 to 9.

21 Claims, 1 Drawing Sheet

COKER/VISBREAKER AND ETHYLENE FURNACE ANTIFOULANT

BACKGROUND OF THE INVENTION

A method for reducing fouling on the surfaces of equipment used in the high temperature treatment of petroleum feedstocks comprising treating the petroleum feedstock with at least 5 parts per million of a compound having the formula:

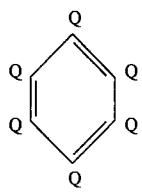

wherein Q is Z, or R with the proviso that two occurances of Q are Z, R is hydrogen, or a straight or branched alkyl group having from 1 to 7 and most preferably from 1 to 4 carbon atoms, and only one or two occurances of R may be alkyl;

Z is represented by the formula:

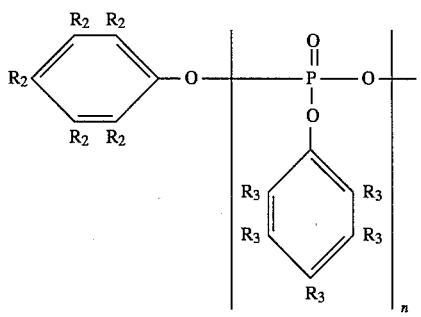

wherein $R_2$ and $R_3$ are the same as R and only one or two occurances of each of $R_2$ or $R_3$ may be alkyl, and "n" is a whole number of from 1 to 9, preferably 1 to 5, and most preferably, "n" is 1 to 3. In an especially preferred embodiment of the invention, "n" is 1, and R, $R_2$ and $R_3$ represent hydrogen.

INTRODUCTION

This invention relates to a method of treating petroleum fractions processed at high temperatures to minimize the formation of foulants and coke. The term "petroleum fractions" embraces crude petroleum, residuum feeds, vacuum residuum, and other heavy petroleum fractions which are heated in a manner to obtain lower boiling cracked products or to improve the handling of the material so treated. Likewise, the additives of this invention may be successfully used to reduce fouling in coke in pyrolysis or cracking furnaces used to manufacture ethylene from the various gaseous and liquid petroleum feedstocks. The additives of this invention are phenol phosphate esters represented by the above formula. The phenol phosphate esters of this invention may be monomeric or may be oligomeric as where "n" in the above formula is a whole number greater than about 1.

In the high temperature treatment of crude oil, residual oil, and the like, fouling occurs on furnace coils and transfer line exchangers due to coking and polymer deposition. The fouling problem is a major operational difficulty experienced in running ethylene plants, and in processes where heavy grades of petroleum are treated to reduce their molecular weight or to improve their handling characteristics including but not limited to visbreakers, delayed or fluid coking operations, and other processes. Depending on deposition rate, furnaces used for cracking petroleum feedstocks including ethylene plants, visbreakers, and the like, all must be periodically shut down for cleaning. In addition to periodic scheduled cleaning, shut downs are sometimes required due to dangerous increases in pressure or temperatures resulting from deposit build-up on furnace coils and transfer line exchangers. Cleaning operations are expensive, both from a time and labor standpoint, and are typically carded out either mechanically or by steam/air decoking.

Various additives have been used to attempt to minimize the formation of foulants in the high temperature processing of crude oil fractions. Among the materials that have been suggested include mono- and di- alkyl, aryl, alkaryl, cycloalkyl, alkenyl, and aralkyl phosphate esters, such as those exemplified in U.S. Pat. No. 4,105,540, which is hereinafter incorporated by reference into this specification. Other materials which have been used include dialkyl acid phosphate or phosphate esters in combination with thiodipropionates, such as those exemplified in U.S. Pat. No. 4,226,700, which is also hereinafter incorporated by reference into this specification and the mono- and di- phosphate and phosphate esters disclosed in U.S. Pat. Nos. 4,024,048, 4,024,049, 4,024,050 and 4,024,051, which are also each hereinafter incorporated by reference into this specification. While these phosphate materials have been generally successfully employed, in some operations use of these materials have proven unsatisfactory, leading to the occurrence of corrosion in units which have been so treated. It is theorized that while effective as antifoulants, the mono- and di- phosphate and phosphite esters suggested by the prior art hydrolyze at high temperatures yielding acidic corrosion products. In my copending related application, Ser. No. 08/242,222, filed May 13, 1994, I disclosed the use of certain t-butyl phosphate esters as antifoulants. Surprisingly, we have found that compounds having the formula:

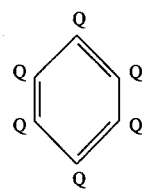

wherein Q is Z, or R with the proviso that two occurances of Q are Z, R is hydrogen, or a straight or branched alkyl group having from 1 to 7 and most preferably from 1 to 4 carbon atoms, and only one or two occurances of R may be alkyl;

Z is represented by the formula:

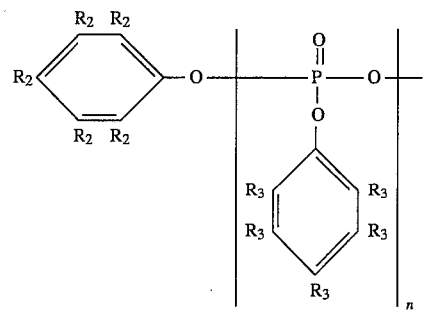

wherein $R_2$ and $R_3$ are the same as R and only one or two occurances of each of $R_2$ or $R_3$ may be alkyl, and "n" is a whole number of from 1 to 9, preferably 1 to 5, and most preferably, "n" is 1 to 3. In an especially preferred embodiment of the invention, "n" is 1, and R, $R_2$ and $R_3$ represent hydrogen.

The antifoulant materials of this invention provide to the art superior antifoulant properties, while at the same time are surprisingly stable to degradation at elevated temperatures encountered in the processing of hydrocarbons.

OBJECTS

It is therefore an object of this invention to provide to the art a method for preventing and inhibiting the formation of foulants on surfaces in contact with hydrocarbon fluids.

It is a further object of this invention to provide to the art a method for inhibiting fouling in the high temperature processing of hydrocarbon fluids especially crude oil fractions.

It is yet a still further object of this invention to provide to the art a method for preventing fouling in the high temperature sections of hydrocarbon processing equipment, including visbreakers, coke drums, ethylene furnaces, preheaters, and the like, using an effective amount of an antifoulant material having the formula:

Further objects will appear hereinafter.

BRIEF DESCRIPTION OF THE INVENTION

Figure 1:
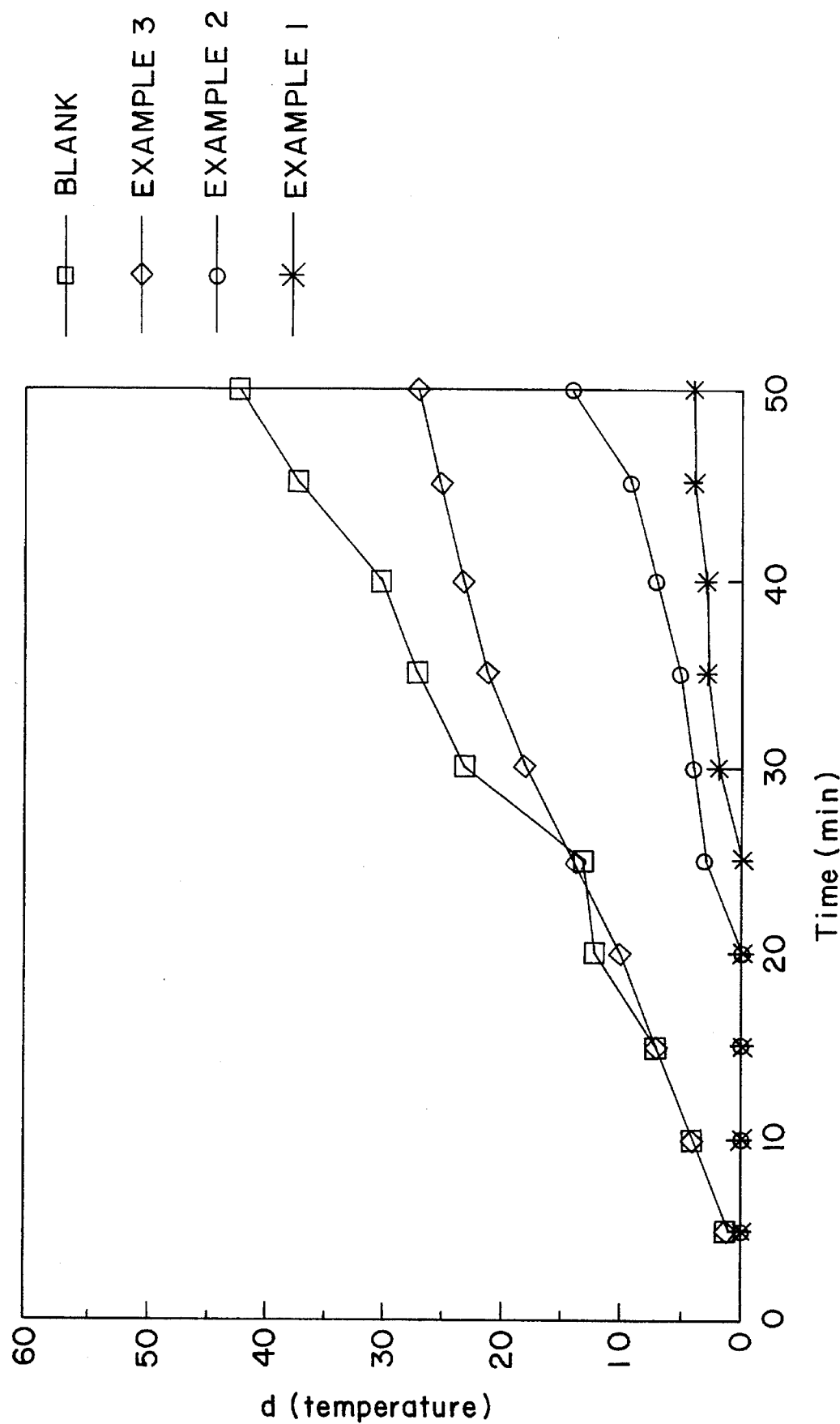
FIG. 1 is a graph comparing the efficacy of several compounds of the instant invention with a commercially available aliphatic phosphate ester. The Fig will be explained in more detail under the heading "Examples".

This invention is accordingly directed to a method of preventing fouling and coke formation on the high temperature sections of hydrocarbon processing equipment in contact with a hydrocarbon fluid which comprises adding to the hydrocarbon fluid prior to its contact with the high temperature sections of such hydrocarbon processing equipment an effective amount of a compound having the formula:

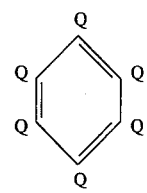
(I)

wherein Q is Z, or R with the proviso that two occurances of Q are Z, R is hydrogen, or a straight or branched alkyl group having from 1 to 7 and most preferably from 1 to 4 carbon atoms, and only one or two occurances of R may be alkyl;

Z is represented by the formula:

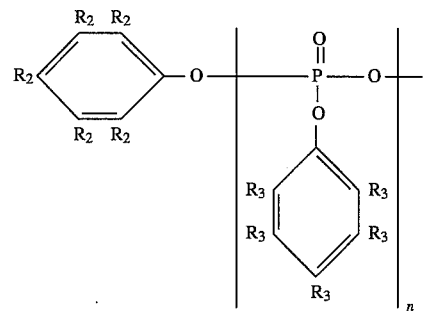

wherein $R_2$ and $R_3$ are the same as R and only one or two occurances of each of $R_2$ or $R_3$ may be alkyl, and "7n" is a whole number of from 1 to 9, preferably 1 to 5, and most preferably, "n" is 1 to 3. In an especially preferred embodiment of the invention, "n" is 1, and R, $R_2$ and $R_3$ represent hydrogen.

THE INVENTION

Compounds falling within the formula of the present invention are commercially available. Among the available materials is a product designated LDP-301 from the FMC Corporation. This product is believed, by chemical analysis to be a compound having the Formula II with a small amount of the structure of Formula III.

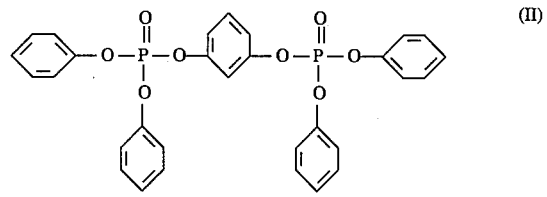
(II)

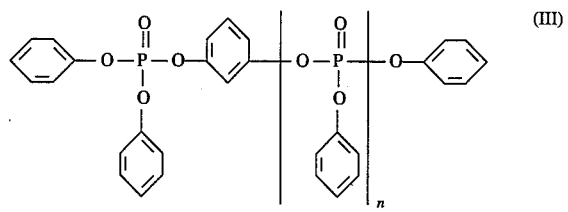
(III)

LDP-301 is stated by its manufacture to be useful as a fire resistant base fluid or highly stable antiwear additive. LDP-301 is also recommended for use as an additive in carboxylic ester base fluids. LDP-301 is stated to have the following physical properties:

| Typical Properties | Test Method | |
|---|---|---|
| Appearance | Visual | clear to amber viscous liquid |
| Odor | Olfactory | None |
| Color | APHA | 500 max |
| Viscosity, cSt @ 100° F. | ASTM-D445 | 140–155 |
| cSt @ 210° F. | | 10–12 |
| Total Acid Number, mgKOH/g | ASTM-D974 | 0.20 max |
| Specific Gravity @ 20/20° C. | ASTM-D1298 | 1.20–1.35 |
| Water Content | ASTM-D1744 | 0.1 max |
| Flash Point, °C.(°F.), COC | ASTM-D92 | >300 (>572) |
| Fire Point, °C.(°F.) | ASTM-D92 | >300 (>572) |
| Autoignition Temp., °C.(°F.) | ASTM-E659 | 640 (1180) |
| Onset of Oxidation by DSC, °C.(°F.) | ASTM-D3350 | >350 (>644) |
| Weight Loss by TGA, °C.(°F.) | ASTM-3850 | |
| 5% weight loss | | 365 (690) |
| 10% weight loss | 400 (752) | |
| Four Ball Wear Data, wear scar in mm (40 kg, 1200 rpm 75° C., 1 hr) | ASTM-D2266 | |
| Polyol ester reference | | 0.76 |
| Polyol + 2% LDP-301 | | 0.44 |
| Diester reference fluid | | 0.92 |
| Diester + 2% LDP-301 | | 0.45 |

While t-butyl and non-substituted trimer phosphate ester materials are exemplified in related application Ser. No. 08/242,222, filed May 13, 1994 which is hereinafter incorporated by reference into this specification, it has now been shown that other that monomeric and oligomeric phenyl phosphate ester materials such as those described in the instant application have superior activity as refinery antifoulant materials.

In the process of this invention the antifoulant materials represented by Formula I are generally added to a petroleum fraction or distillate that will be subjected to a high temperature processing operation in an amount to provide from 5 to 2000 and preferably 50 to 2000 ppm of active phosphate ester material. Most preferably, from 200 to 1000 ppm of the compounds represented by Formulas I are added to the hydrocarbon stream prior to its introduction into the high temperature processing area where it will be subjected to relatively severe conditions that can lead to the formation of polymer or coke. The additives of this invention are generally soluble in the hydrocarbon fluid to which it is applied, and in order for ease of application, may be diluted with common solvents, such as kerosene, heavy aromatic naphtha, or the like prior to its introduction into the system. Surprisingly, the material acts as an antifoulant in the high temperature processing of petroleum fractions to which it is added. By high temperature processing is meant temperatures ranging from as low as 100° C, the boiling point of water to 1000° C. or higher. Generally, the additive of this invention is added to hydrocarbon fluids which will be subjected to temperatures in excess of 330° C., (626° F) at atmospheric pressure, the approximate temperature at which thermal cracking is initiated.

As stated earlier, the antifoulant process of this invention is applicable to a wide range of hydrocarbon processing operations that are conducted at high temperature. Among the hydrocarbon processing operations to which this invention may find applicability are those operations where high molecular weight materials are cracked to produce lower molecular weight materials or to decrease their viscosity. These operations include hydrocracking, coking, visbreaking, steam cracking, reforming, and the like. The materials may also be used in the feed materials going to pyrolysis or cracking furnaces to manufacture ethylene, and the like. The additives may be added to delayed cokers, preheaters, furnaces, and other sections where hydrocarbon fluids are processed at high temperatures. The additives may further be added to the hydrocarbon fluid effluent coming out of any of the above described operations. The addition of the compounds of this invention to the effluent from a high temperature process section is thought to be particularly beneficial since it is thought that the high temperature sections destabilize certain components in the hydrocarbon fluids so treated and that the additive of this invention acts to prevent coke and foulant formation on the equipment sections that are contacted with the hot hydrocarbon fluids as they exit the heated sections.

The present invention characteristically may be practiced advantageously with any crude oil material, such as one selected from the group consisting of crude oils and reduced crude oils.

Typically, the phosphate ester materials of this invention are added to a crude oil material at a lower level of from about 5 parts per million total weight basis to about 2000 parts per million total weight basis as the upper limit. It should be pointed out the upper limit will be limited by economics, and not the effect of the additive, and quantities greater than 2000 parts per million of the additive may be added. Preferably, the total amount of the additive of this invention added to the hydrocarbon fluid material ranges from about 5 to 2000 parts per million (same basis). In the processing of crude oils, heating times can vary enormously, as those skilled in the art of petroleum refining will readily appreciate, but are generally in the range of about from a few second to several hours, though longer and shorter time can be involved.

As used herein, the term "crude oil" can be considered to have reference to materials used as starting feedstocks for a petroleum crude oil refining operation, such as a petroleum having a substantially naturally occurring composition and which composition has not been appreciably altered through the use of distillation or pyrolysis. Examples of crude oils include many materials, such as refinery battery limit crudes (e.g. a crude as it exists in storage vessels preceding refining), degassed crude oils (e.g., a crude which has been stripped at temperatures typically in excess of from about 75° to 125° F. to remove therefrom low boiling hydrocarbons, such as lower alkanes and other low volatiles), tar sand crudes (e.g., a product obtained from a destructive distillation of a tar sand), condensate crudes (e.g., a crude obtained by condensation of heavy ends from a natural gas well), shale oils, (e.g., a crude oil obtained from a natural gas well), shale oils, (e.g., a crude oil obtained from oil shale by destruction distillation followed by hydrotreating), desalted crude oils (e.g., a crude oil which has been subjected to a procedure whereby the content of mineral salts present in a starting crude oil is reduced typically to a salt content not above 5 pounds per 1000 barrels, although the amount of salt remaining in de-salted crude can vary widely as those skilled in the art of petroleum sometimes overlap on one another and are not well defined. Presently preferred crude oil starting feedstocks for the present invention include battery limit crude oil, degassed crude oil, and desalted crude oil.

Similarly, as used herein, the term "reduced crude oil" can be considered to have reference to a starting crude oil feedstock which has been subjected to distillation at temperatures which are generally above those employed for making a degassed crude oil using temperatures as above indicated, such as a residual crude oil (usually a liquid) which has not been substantially altered except as a result of heating and removing material therefrom by distillation of pyrolysis. Examples of reduced crude oil include a wide variety of materials, as those skilled in the refinery art will appreciate readily, such as topped crude oils (e.g., a product which results after gas oils boiling in the range of from about 400° to 575° F. have been removed from a crude oil by fractional distillation), atmospheric residues (e.g., a product which results from the fractional distillation of a crude oil in an atmospheric pipe still and which boils above a temperature in the range of from about 350° to 650° F.), viscous pitches (e.g., a product which results from a fractional distillation of an atmospheric residue in a vacuum still and which boils above a temperature in the range from about 1000° to 1500° F. at pressures of from about 1 to 5 psig). Viscous pitches can be considered to include coker feedstocks. Presently preferred reduced crude oils include topped crude oils, atmospheric residues and viscous pitches.

The processing of crude oil materials in a refinery is a relatively well developed art. Characteristically and usually, the processing of crude petroleum comprises a successive series of steps. These steps characteristically and preferably are as follows:

A. heating a crude oil in at least one heat exchanger to a temperature typically in the range from about 100° to 200° F., B. desalting the crude oil typically and preferably by the substeps of
  (1) turbulently mixing the crude oil which has been preferably first pre-heated as above indicated as typically from about 3 to 8 parts by weight of water for each 100 parts by weight of such crude oil to form an emulsion of the water in oil type,
  (2) breaking said emulsion through the use of chemical agents, electrical means, or some combination thereof; and
  (3) separating the resulting aqueous phase from the resulting crude oil phase, C. further heating the resulting crude oil in at least one post desalter heat exchanger to a temperature typically in the range from about 200° to 500° F., D. still further heating the resulting crude oil in a furnace to a temperature typically in the range from about 500° to 700° F., E. charging the so-heated crude oil to an atmospheric still wherein such crude oil is progressively fractionally distilled at temperatures typically in the range from about 300° to 650° F. under pressures typically ranging from and including atmospheric up to about 50 p.s.i.a. and collecting the distillates until an atmospheric residue results which boils above a temperature typically in the range of from about 300° to 650° F., F. heating said atmospheric residue in a vacuum furnace to a temperature typically in the range from 650° to 800° F. while maintaining a subatmospheric pressure of from about 5 to 14 p.s.i.a. typically, G. charging the so-heated atmospheric residue to a vacuum still wherein such atmospheric residue is progressively fractionally distilled at a temperature typically in the range from about 800° to 1100° F. under pressure typically ranging from about 1 to 5 p.s.i.a. and collecting distillates until a viscous pitch results typically boiling in the range from about 1000° to 1500° F. at a sub-atmospheric pressure of typically from about 1 to 5 p.s.i.a., and H. progressively heating the viscous pitch in a zone at temperatures typically ranging from about 860° to 900° F. at pressures typically ranging from about 50 to 350 psig for a time ranging from about 1 second to ½ hours.

In the case of step (H), the heating can occur either in a coker zone or in a thermal cracking zone. In the case of a coker zone, the heating is pyrolytic, and the distillates are collected, until a final solid residue is obtained which is a coke. In the case of a thermal cracking zone, the process involved is termed "visbreaking" and the distillates are collected without changing the fluid nature of the starting viscous pitch (as by forming coke). Residence times of the charged material (initially viscous pitch) in a coker zone typically extends for periods of time more than 10 seconds with common coking times ranging from about 45 minutes to 4 ½ hours. Residence times of starting pitch in a visbreaking operation in a thermal cracking zone typically are shorter than about 10 seconds maximum.

In the crude oil processing steps above described, a coker furnace can follow step (G) and precede step (H) so that after step (G) the following processing step sequence occurs after step (G) in place of step (H):

H' heating said viscous pitch in a furnace to a temperature in the range from about 1000° to 1500° F. (538° C.–816° C.) at near atmospheric pressure and r passing said so heated pitch into a flash zone at temperatures typically in the range from about 860° to 900° F. at pressures typically of from about 50 to 350 p.s.i.g. Such flash zone can either be a coker zone or a visbreaking zone, as above indicated. If a coker zone, residence time in such zone is prolonged and pyrolysis occurs. If a visbreaker zone, residence time is brief and cracking occurs, giving rise to naphtha and gas oil as lighter products and producing a residuum which is less viscous than the charge stock.

These crude oil and reduced crude oil processing steps, as indicated, are well known to the art of petroleum refining and do not constitute as such part of the present invention. Those skilled in the art will appreciate that many variation, etc., can be used in any given hydrocarbon processing operation, involving, for examples, additional steps, substitute steps, recycle loops, and the like. The above summary is merely representative, but characteristic, of the sequence of steps typically found in a refinery when processing crude oil. Petroleum processing is discussed in such reference works as that by Nelson entitled "Petroleum Refinery Engineering", see, for example, chapter 7, pp. 248–260; chapter 8, pp. 265–268; chapter 17, pp. 547–554 and chapter 19, pp. 678–693. All such crude oil processing steps characteristically cause fouling of hydrocarbon processing equipment in absence of an additive or the like, as those skilled in the art well appreciate.

Fouling deposits apparently occur most frequently at temperatures between about 200° and 1800° F. (93°–982° C.), or even higher such as in, for example, certain ethylene furnaces.

The types of equipment affected most frequently include heat exchange surfaces, such as indicated above. The fouling deposits themselves are typically and principally polymerization products and are characteristically black in color. Some are initially gummy masses which convert to coke-like masses at elevated temperatures. Inorganic portions of such deposits frequently contain components, such as silica, iron-oxides, sulfur oxides, iron sulfides calcium oxide, magnesium oxide, inorganic chloride salts, sodium oxide, alumina, sodium sulfate, copper oxides, copper salts, and the like. These deposits are not readily solubilized by common organic solvents and these deposits are distinguishable from the corrosion and sludge formation sometimes occurring in finished products. Conventional antioxidants, stabilizing chemicals, and the like are characteristically relatively ineffective as antifoulants.

During a distillation or pyrolysis carded out with a crude oil material containing formula (1) and/or (2) material, this additive material is characteristically not carded over in the vapors evolved, but remains instead with the residue (reduced crude oil) involved. Chemical and physical changes may occur, of course, in such additive material during a given distillation or pyrolysis operation, but it is now theorized (and there is no intent herein to be found by theory) that by-products, degradation products, and the like, are not appreciably carded over with a vapor phase stream removed during a distillation or pyrolysis operation from a reduced crude oil.

MIXING AND THE COMPOSITIONS

Only relatively small amounts of the additives of this invention are used to produce a reduction both in fouling deposits, and/or a suppression of fouling material in the typical practice of this invention. Preferable, the total amount of phosphate ester compound present in a total mixture ranges from about 5 to 2000 parts per million by weight, and more preferably ranges from about 50 to 1000 parts per million, though larger and smaller amounts of such esters may be employed, as those skilled in the art will appreciate. Owing to the complexity of the variables involved, it is not possible to indicate optional concentrations of additives for all possible use situations.

The compounds of this invention are well suited for use with heat transfer surfaces of ferrous metals (such as stainless steel or carbon steel) or of aluminum and appear to be particularly effective as antifoulants at tube wall temperatures below about 1400° F. and at oil temperatures below about 600° F. to 950° F., (315° C.–510° C.) although they can be used as antifoulants at higher temperatures, as taught herein.

In another preferred mode of practicing this invention, the phosphate ester additives of this invention may be added to a crude oil material being processed in previously fouled hydrocarbon processing equipment to achieve a reduction in the fouling of such equipment. Such a reduction is shown in such ways as reduced pressure drop across a given unit or zone, increased temperature (better heat transfer) across a given trait (such as a heat exchanger) or zone, reduced furnace fuel consumption, and the like.

Mixing of the phosphate ester materials of this invention with the hydrocarbon fluid may be accomplished by any convenient or conventional means before or during a heating of such materials. Typically, the phosphate ester compound is injected through a chemical feed pump or the like ahead of the heat exchangers subject to fouling, or the like. Preferable, injection takes place as far back in a system as possible. To assure substantially complete dispersion, a suitable injection point should be selected, such as into the suction region of a charge pump. Sleeve type arrangements termed "quills" may be preferably used to inject additives into process streams which extend into a line to cause better mixing. The phosphate ester compound of the invention is preferably fed in solution form using a liquid which is soluble or miscible with the mineral hydrocarbon mixture being treated. When large pump feeding rates are involved, one may employ more dilute solutions than at lower pumping rates.

The solvent used to prepare a solution of the phosphate ester compounds of this invention can vary widely. In general, the solvent should have higher boiling point higher than that of the more volatile components of the process stream into which the resulting solution is to be injected. A presently preferred type of solvent is one which has a boiling point high enough to be suitable for many injection locations, such as a heavy aromatic hydrocarbon mixture (of the type derived from petroleum refining) having a boiling point in the range from about 350° to 550° F. Preferably such solvent should have a sulfur content not greater than about 1 weight percent (based on total solvent weight). Typically and preferably such a solvent is comprised of at least 90 weight percent (total solvent weight basis) of six membered aromatic tings which may each be substituted by at least one alkyl group having from 3 through 7 carbon atoms each, as those skilled in the art will appreciate. The total amount of phosphate ester dissolved a given solution can vary widely, but usually and conveniently falls in the range of from about 10 to 40 percent by weight.

When the phosphate ester materials of this invention are fed to a stream having a temperature above about 200° F., it is preferred to have a nipple connecting the feedline to the process line which is made of stainless steel. For best results, the equipment is preferable initially thoroughly cleaned, most preferably by mechanical means. Starting charge dosages are often greater than subsequent dosages.

In one preferred mode of practicing this invention, at a given injection point, an initial dosage rate of from about 5 to 2000 parts per million of the phosphate ester is used. After an operational period of, for example, about 1 to 2 weeks, this dosage rate can often be reduced to a level of from about 5 to 1000 parts per million with no decrease in antifoulant activity.

In another preferred mode of practicing the present invention, the phosphate ester materials of the invention are mixed simultaneously with a crude oil material feed stream being processed at various successive locations thereamong. For example, such ester material can be first injected into and mixed with a crude oil stream before such undergoes the initial heating which is identified about as step (A). Thereafter, and simultaneously, such material may also be injected into a process stream before each of the steps identified above as steps (B) through (H) using a same or similar rate of addition at each injection location. If such material is not so injected at each such location, it is preferred to inject such at least before steps (A), (C), (F) and (H).

EXAMPLES

In order to demonstrate the effectiveness of the materials of this invention the following examples were conducted. The test work was conducted and hot liquid process simulator HLPS model 330 available Alcor Inc., Tex. The HLPS may generally be described as a tube-in-shell heat exchanger test apparatus having the ability to monitor changes in both temperature and pressure. The apparatus generally consists of a heated sample reservoir, allowing flow to pass across a heated test section. The sample is then returned to the reservoir. As fouling occurs, deposition is laid down on the interior of the test section, and more heat input is then required to maintain a constant temperature of the sample across the test section.

LDP-301 was evaluated on a heavy vacuum gas oil obtained from a commercial refinery in Oklahoma. The test unit was operated under the following conditions:

| | |
|---|---|
| Initial Rod temperature | 1000° F. |
| Setpoint temperature | 750° F. |
| Pressure | 300 psig |
| Reservoir temperature | 100° C. |
| Line temperature | 100° C. |
| Pump block temperature | 100° C. |

Three samples were evaluated trader these conditions. A blank, with no chemical additive, 3000 ppm of the tri-t-butyl phenol phosphate ester described in related application Ser. No. 08/242,222, filed May 13, 1994 (hereinafter labeled Example 2), 3000 ppm of a commercially available dialkyl phosphate ester antifoulant material of the type described in U.S. Pat. No. 4,105,540, and 3000 ppm of the additive of this invention labeled "Example 1". Results of the testing are shown in FIG. 1. From the Alcor graph found as FIG. 1, the compound of the invention outperformed Examples 2 and 3.

Viewing the Figure, wherein the "X" axis is time in minutes, and the "y" axis is difference in temperature between the robe and outer wall, the vacuum gas oil treated with the material of this invention exhibited substantially less temperature variance, even over a 50 minute time period as compared to the other additives tested, or the vacuum gas oil with no additive.

I claim:

1. A method of preventing fouling and coke formation on the high temperature sections of hydrocarbon processing equipment in contact with a hydrocarbon fluid which comprises adding to the hydrocarbon fluid prior to its contact with the high temperature sections of such hydrocarbon processing equipment an effective amount of a compound having the formula:

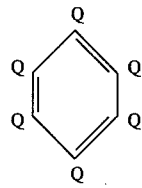

wherein Q is Z, or R with the proviso that two occurances of Q are Z, R is hydrogen, or a straight or branched alkyl group having from 1 to 7 carbon atoms, and only one or two occurances of R may be alkyl;

Z is represented by the formula:

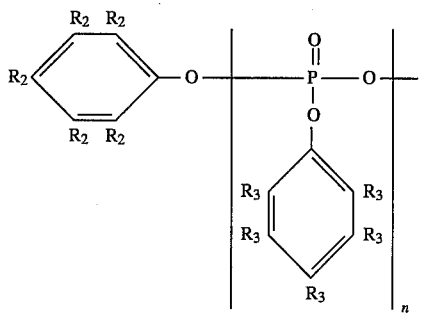

wherein $R_2$ and $R_3$ are the same as R and only one or two occurances of each of $R_2$ or $R_3$ may be alkyl, and "n" is a whole number of from 1 to 9.

2. The method of claim 1 wherein the high temperature section of the hydrocarbon processing equipment is at a temperature of from about 330° C. to about 1000° C.

3. The method of claim 1 wherein from 5 to 2000 ppm of the compound is added to the hydrocarbon fluid.

4. The method of claim 1 wherein the hydrocarbon processing equipment is selected from the group consisting of visbreakers, delayed cokers, preheaters, furnaces, and/or the effluent therefrom.

5. The method of claim 1 wherein "n" is a whole number of from 1 to 5.

6. The method of claim 1 wherein "n" is a whole number of from 1 to 3.

7. The method of claim 1 wherein "n" is 1.

8. The method of claim 1 wherein "n" is 1 and each occurrence of $R_1$, $R_2$, and $R_3$ is hydrogen.

9. A method of preventing fouling and coke formation on the surfaces of hydrocarbon processing equipment in contact with a hydrocarbon fluid at a temperature of about 330° C. to 1000° C. which comprises adding an effective amount of a compound of the following formula to the hydrocarbon fluid prior to its contacting such hydrocarbon processing equipment:

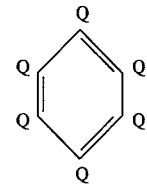

wherein Q is Z, or R with the proviso that two occurances of Q are Z, R is hydrogen, or a straight or branched alkyl group having from 1 to 7 carbon atoms, and only one or two occurances of R may be alkyl;

Z is represented by the formula:

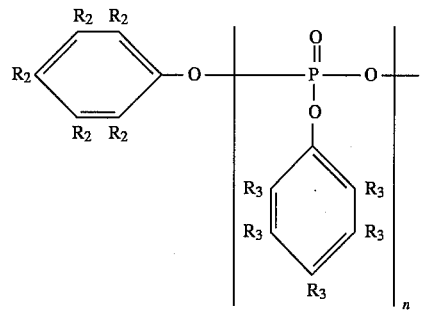

wherein $R_2$ and $R_3$ are the same as R and only one or two occurances of each of $R_2$ or $R_3$ may be alkyl, and "n" is a whole number of from 1 to 9.

10. The method of claim 8 wherein from 5–2000 ppm of the hydrocarbon fluid.

11. The method of claim 8 wherein the hydrocarbon processing equipment is selected from the group consisting of visbreakers, delayed cokers, preheaters, furnaces, and/or the effluent therefrom.

12. The method of claim 8 wherein "n" is a whole number of from 1 to 5.

13. The method of claim 8 wherein "n" is a whole number of from 1 to 3.

14. The method of claim 9 wherein "n" is 1, and each occurrence of R, $R_1$, and $R_2$ is hydrogen.

15. The method of claim 9 wherein "n" is a whole number of from 1 to 3 and "R" is a hydrogen or an alkyl group containing from 1 to 4 carbon atoms with at least one occurrance of "R" being alkyl.

16. The method of claim 9 wherein the compound is added to the hydrocarbon fluid prior to its introduction into an ethylene furnace.

17. The method of claim 9 wherein the compound is added to the hydrocarbon fluid prior to its introduction into a visbreaker.

18. A petroleum distillate containing 1–2000 ppm of an antifoulant of the formula:

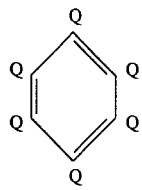

wherein Q is Z, or R with the proviso that two occurances of Q are Z, R is hydrogen, or a straight or branched alkyl group having from 1 to 7 carbon atoms, and only one or two occurances of R may be alkyl;

Z is represented by the formula:

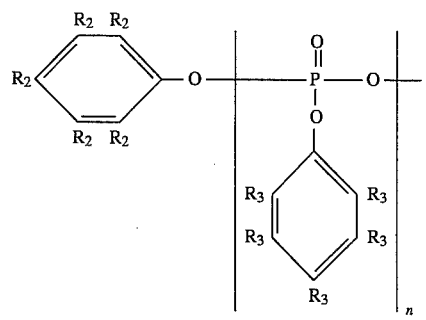

wherein $R_2$ and $R_3$ are the same as R and only one or two occurances of each of $R_2$ or $R_3$ may be alkyl, and "n" is a whole number of from 1 to 9.

19. The petroleum distillate of claim 18 wherein "n" is a whole number of from 1 to 5.

20. The petroleum distillate of claim 18 wherein "n" is a whole number of from 1 to 3.

21. The petroleum distillate of claim 18 wherein "n" is 1, and each occurrence of R, $R_2$, and $R_3$ are hydrogen.

* * * * *

UNITED STATES PATENT AND TRADEMARK OFFICE
CERTIFICATE OF CORRECTION

PATENT NO. : 5,460,712
DATED : 10/24/95
INVENTOR(S) : HARALD K. LEMKE

It is certified that error appears in the above-indentified patent and that said Letters Patent is hereby corrected as shown below:

```
COLUMN 12, CLAIM 4, LINE 7-8 of visbreakers, delayed cokers, preheater, furnaces,
and/or the effluent therefrom.

should read

-- of visbreakers, delayed cokers, preheaters and furnaces.--
```

Signed and Sealed this

Twenty-seventh Day of May, 1997

*Attest:*

BRUCE LEHMAN

*Attesting Officer*   Commissioner of Patents and Trademarks